(12) United States Patent
Smith et al.

(10) Patent No.: US 8,758,359 B2
(45) Date of Patent: Jun. 24, 2014

(54) INSTRUMENTS FOR IMPLANTING IMPLANTABLE PROSTHESES

(75) Inventors: Daniel J. Smith, Dayton, NJ (US); Allison London Brown, New Hope, PA (US); Marcus Carey, Victoria (AU); David Robinson, Far Hills, NJ (US)

(73) Assignee: Ethicon, Inc., Somerville, NJ (US)

( * ) Notice: Subject to any disclaimer, the term of this patent is extended or adjusted under 35 U.S.C. 154(b) by 1549 days.

(21) Appl. No.: 11/748,144

(22) Filed: May 14, 2007

(65) Prior Publication Data

US 2008/0287956 A1 Nov. 20, 2008

(51) Int. Cl.
*A61B 17/58* (2006.01)
*A61F 2/02* (2006.01)

(52) U.S. Cl.
USPC .............................. 606/99; 600/30

(58) Field of Classification Search
CPC ................ A61F 2/0045; A61F 2002/0072
USPC ................. 606/99, 205; 600/29–30
See application file for complete search history.

(56) References Cited

U.S. PATENT DOCUMENTS

| | | | | |
|---|---|---|---|---|
| 3,628,522 A | * | 12/1971 | Kato | 600/564 |
| 4,307,716 A | | 12/1981 | Davis | |
| 5,228,451 A | * | 7/1993 | Bales et al. | 600/564 |
| 5,258,005 A | * | 11/1993 | Christian | 606/205 |
| 5,324,293 A | * | 6/1994 | Rehmann | 606/85 |
| 5,423,855 A | * | 6/1995 | Marienne | 606/208 |
| 5,472,439 A | * | 12/1995 | Hurd | 606/1 |
| 5,735,857 A | * | 4/1998 | Lane | 606/99 |
| 5,782,830 A | * | 7/1998 | Farris | 606/99 |
| 5,830,215 A | * | 11/1998 | Incavo et al. | 606/79 |
| 5,993,474 A | * | 11/1999 | Ouchi | 606/206 |
| 6,131,576 A | | 10/2000 | Davis | |
| 6,136,017 A | * | 10/2000 | Craver et al. | 606/205 |
| 6,190,381 B1 | * | 2/2001 | Olsen et al. | 606/32 |
| 6,216,353 B1 | | 4/2001 | Schenck | |
| 6,216,698 B1 | | 4/2001 | Regula | |

(Continued)

FOREIGN PATENT DOCUMENTS

| | | |
|---|---|---|
| DE | 3720858 A | 1/1989 |
| DE | 296 04 657 U | 5/1996 |

(Continued)

OTHER PUBLICATIONS

English translation of DE 202007001802.*
Samuelsson, E.C. et al. "Signs of genital prolapse in a Swedish population of women 20-59 years of age and possible related factors", Am. J. Obstet Gynecol. 180:299-305 (1999).

(Continued)

*Primary Examiner* — Kevin T Truong
*Assistant Examiner* — Christian Sevilla

(57) ABSTRACT

An instrument including a grip portion, a first substantially rigid extension arm projecting outwardly from the grip portion along a first longitudinal axis, and a second substantially rigid extension arm projecting outwardly from the grip portion along a second longitudinal axis. The first has a straight portion adjacent the grip portion that lies substantially within a first plane, and a distal portion extending from the straight portion to a first distal end along a length of which the first extension arm extends upward relative to the first plane and rotates about its first longitudinal axis. The second has a second straight portion adjacent the grip portion that lies substantially within the first plane, and a second distal portion extending from the straight portion to a second distal end along a length of which the second extension arms extends downward relative to the first plane and rotates about its longitudinal axis.

8 Claims, 7 Drawing Sheets

(56) References Cited

U.S. PATENT DOCUMENTS

| | | | |
|---|---|---|---|
| 6,319,257 B1 * | 11/2001 | Carignan et al. | 606/99 |
| 6,543,141 B1 | 4/2003 | Biehl | |
| 2002/0028980 A1 | 3/2002 | Thierfelder et al. | |
| 2002/0045904 A1 * | 4/2002 | Fuss et al. | 606/99 |
| 2002/0083949 A1 | 7/2002 | James | |
| 2004/0030346 A1 * | 2/2004 | Frey et al. | 606/99 |
| 2004/0147936 A1 * | 7/2004 | Rosenberg et al. | 606/99 |
| 2005/0000523 A1 | 1/2005 | Beraud | |
| 2005/0016545 A1 | 1/2005 | Nissenkorn | |

FOREIGN PATENT DOCUMENTS

| | | | | |
|---|---|---|---|---|
| DE | 29604657 | * | 6/1996 | A61C 3/00 |
| DE | 20 2007 001802 U | | 4/2007 | |
| DE | 202007001802 | * | 4/2007 | A61C 19/00 |
| FR | 2 852 813 A | | 10/2004 | |
| RU | 2209605 C2 | | 7/2001 | |
| WO | WO 01/06951 A1 | | 2/2001 | |
| WO | WO 02/078552 A1 | | 10/2002 | |
| WO | WO 02/078568 A1 | | 10/2002 | |
| WO | WO 03/028585 A2 | | 4/2003 | |
| WO | WO 2004/045457 A1 | | 6/2004 | |

OTHER PUBLICATIONS

Olsen, A.L. et al. "Epidemiology of Surgically Managed Pelvic Organ Prolapse and Urinary Incontinence", Obstet Gynecol vol. 89, No. 4, 501-506 (1997).

Winters, J. C. et al. "Abdominal Sacral Colpopexy and Abdominal Enterocele Repair in the Management of Vaginal Vault Prolapse", Urology 55-63 (2000).

Deval, B. et al. What's new in prolapse surgery? Current Opinion in Urology 13:3-15-323 (2003).

Maher, C.F. et al., "Abdominal sacral colpopexy or vaginal sacrospinous colpopexy for vaginal vault prolapse: A prospective randomizer study", Am. J. Obstet Gynecol 190:20-26 (2004).

Cervigni, M. et al. "The use of synthetics in the treatment of pelvic organ prolapse. Current Opinion in Urology" 11:429-435 (2001).

Visco, A.C. et al., "Vaginal mesh erosion after abdominal sacral colpopexy", Am. J. Obstet Gynecol 184:297-302 (2001).

Boyles, S. H. et al., "Procedures for pelvic organ prolapse in the United States 1979-1997", American Journal of Obstetric Gynecology 188: 108-115 (2003).

Pang, Man-Wah, et al. "An overview of pelvic floor reconstructive surgery for pelvic organ prolapse", Journal of Pediatrics, Obstetrics and Gynecology (2003).

* cited by examiner

INSTRUMENTS FOR IMPLANTING IMPLANTABLE PROSTHESES

BACKGROUND OF THE INVENTION

1. Field of the Invention

The present invention relates to surgical instruments suitable for facilitating the implantation of implantable prostheses, and in particular such prostheses used in repairing various pelvic floor prolapse conditions.

2. Background Discussion

Each year in the USA approximately 200,000 women undergo pelvic organ prolapse surgery. Pelvic organ prolapse generally involves the descent of one or more of the uterus, the bladder or the rectum along the vagina towards (or in extreme cases protruding beyond) the introitus. Women of advancing years, or those that have borne several children are more frequent sufferers of pelvic organ prolapse. Traditional vaginal surgery to address these conditions is associated with a high failure rate of between 30-40%. Complex and elaborate abdominal, vaginal and laparoscopic procedures such as abdominal sacral colpopexy, transvaginal sacrospinous ligament fixation, and laparoscopic sacral colpopexy have been developed to reduce the risk of prolapse recurrence. Unfortunately these procedures require a high level of surgical expertise and are only available to a small number of specialist practitioners and therefore to a small number of patients. Details of various procedures currently in use are described in Boyles S H., Weber A M, Meyn L. "Procedures for pelvic organ prolapse in the United States", 1979-1997, American Journal of Obstetric Gynecology 2003, 188; 108-115.

Recently there has been a trend towards the use of reinforcing materials to support a vaginal wall damaged by prolapse. Prosthetic materials such as donor fascia lata, pig dermis and various types of synthetic mesh have been utilized with mixed success. These materials are generally positioned adjacent to or in contact with the vaginal wall or walls and sutured into position or secured via straps.

WO 2004/045457 discloses a different approach that utilizes a prosthetic material in repairing damaged pelvic tissue, and subsequently inserts an intra-vaginal splint. The splint is placed into the vagina, and operates to reduce the mobility of the vaginal walls during tissue ingrowth. The repairs are typically made by dissecting either the posterior wall of the vagina, the anterior wall of the vagina, or both. A graft of either synthetic material, such as a polypropylene mesh or other fabric, or autologous or analogous material is freely placed without fixation in the dissected area between the vaginal wall and the prolapsing organ. The vaginal incision is then closed by suture or other tissue closure means, at which time the vaginal splint is inserted into the vagina and affixed to both walls at the cervical cuff. The splint stabilizes the vagina, keeps it elongated in its anatomical position, and helps to hold the graft in place by preventing it from sliding or dislodging. Eventually the fascial tissue on each side of the graft will infiltrate into it thereby incorporating it into the body, and the splint can subsequently be removed.

The present invention provides an instrument suitable for facilitating the implantation of prostheses, and in particular prostheses used in procedures such as those described above.

SUMMARY OF THE INVENTION

An instrument is provided for facilitating implantation of an implantable prosthesis. The instrument includes a grip portion having a top side, a bottom side, first and second opposing end sides, and front and rear sides, a first substantially rigid extension arm projecting outwardly from the first end side of the grip portion along a first longitudinal axis, and a second substantially rigid extension arm projecting outwardly from the second end side of the grip portion along a second longitudinal axis. The first substantially rigid extension portion has a straight portion adjacent the grip portion wherein the first extension arm lies substantially within a first plane, and a distal portion extending from the straight portion to a first distal end along a length of which the first extension arm extends upward relative to the first plane and rotates about its first longitudinal axis. The second substantially rigid extension portion has a second straight portion adjacent the grip portion wherein the first extension arms lies substantially within the first plane, and a second distal portion extending from the straight portion to a second distal end along a length of which the second extension arms extends downward relative to the first plane and rotates about its longitudinal axis.

In alternate embodiments, the distal portion of the first and/or second extension arms rotate counterclockwise about respective first and second longitudinal axes.

In yet another embodiment, the distal portion of the first and second extension arms each rotate less than 90 degrees, and may rotate less than 45 degrees.

In yet another embodiment, the longitudinal axes of the first and second extension arms at the first and second distal ends respectfully are substantially perpendicular to the first plane.

In alternative embodiments, the instrument may have one or more of the following: first and second extension arms with a substantially uniform cross-section along their lengths; first and second extension arms with substantially identical lengths, cross-sections, and straight portions, and extension arm cross-sections that are substantially rectangular.

Another instrument for facilitating implantation of an implantable prosthesis is provided including a grip portion, a first substantially rigid extension arm projecting outwardly from a first end side of the grip portion along a first longitudinal axis, and a second substantially rigid extension arm projecting outwardly from a second opposing end side of the grip portion along a second longitudinal axis. The first substantially rigid extension portion extends to a first distal end and includes a distal end portion wherein the first extension arm extends upward relative to the grip portion and rotates about its first longitudinal axis, and the second substantially rigid extension portion extends to a second distal end and includes a second distal portion wherein the second extension arm extends downward relative to the grip portion and rotates about its longitudinal axis.

In yet another embodiment, the instrument includes one or more visual indicators on the first and/or second extension arms for indicating proper orientation of the instrument.

DETAILED DESCRIPTION OF THE INVENTION

Figure 1:
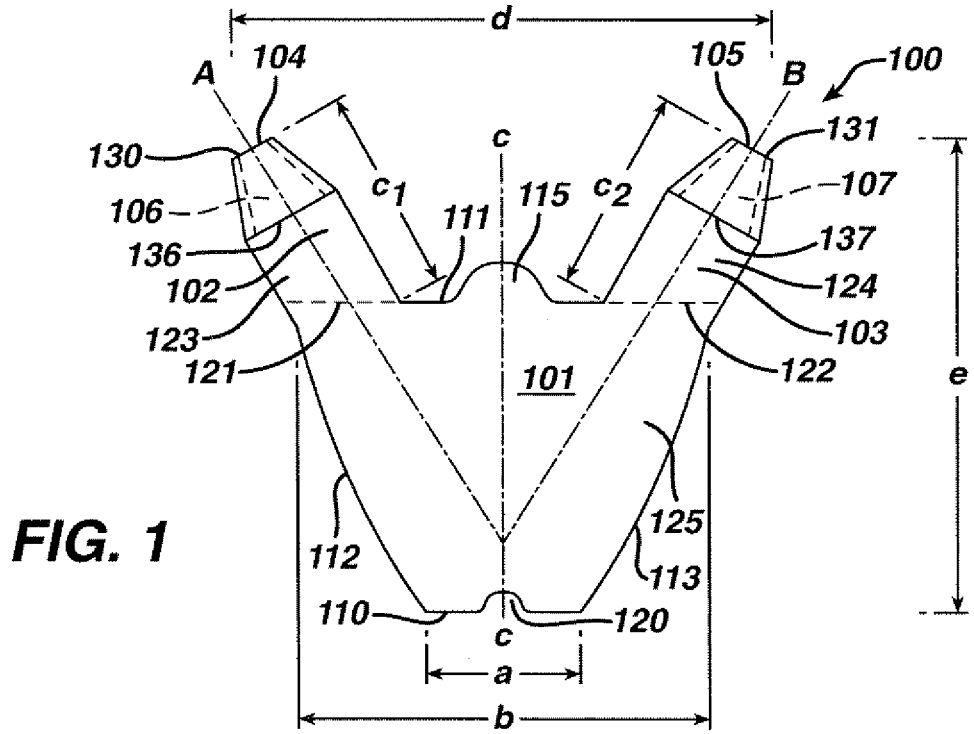
FIG. 1 is a top view illustrating an implant according to the present invention.

Referring now to FIG. 1, an implant 100 is provided having particular application for repair of anterior, posterior and/or apical vaginal defects. The implant may be comprised of any suitable biocompatible material, absorbable or non-absorbable, synthetic or natural or a combination thereof. Preferably the implant is a mesh type material, and in a preferred embodiment, is constructed of knitted filaments of extruded polypropylene, such as that manufactured and sold by Ethicon, Inc. of Somerville, N.J. under the name GYNEMESH PS.

The implant 100 has a central body portion 101 having anterior and posterior edges 110, 111, and first and second lateral side edges 112, 113 that may be slightly arced as shown. The anterior edge 110 has a recess 120 extending inwardly therein and the posterior edge has a tab element 115 extending outwardly therefrom. The recess and tab element are both substantially centrally located along the anterior and posterior edges respectively as shown to aid in properly positioning the implant. In addition, the tab element 115 provides additional material for attachment to the uterus if desired. The central body portion is preferably sized and shaped to be positioned either between the urinary bladder and the upper ⅔ of the vagina, or between the rectum and the upper ⅔ of the vagina as will be described further below.

The implant further has first and second 102, 103 strap-like extension portions extending outwardly from the central body portion to first and second distal ends 104, 105. The strap-like extension portions extend outwardly from first and second end regions 121, 122 of the posterior edge 111 of the central body portion at an angle so as to substantially form a "Y" shaped implant in combination with the central body portion 101. In a preferred embodiment, lines A and B that substantially symmetrically bisect a top surface 123, 124 of the strap-like extension portions, and line C that substantially symmetrically bisects a top surface 125 of the central body portion, intersect within the central body portion as shown in FIG. 1.

Each of the first and second strap-like extension portions 102, 103 each further include a pocket 106, 107 at their respective distal ends. Each pocket has a closed end 130, 131 substantially adjacent to the distal ends 104, 105 of the strap-like extension portion, two closed sides, and an open end 136, 137 proximal of the closed end, with the open end opening toward the central body portion 101 as illustrated.

Figure 2A:
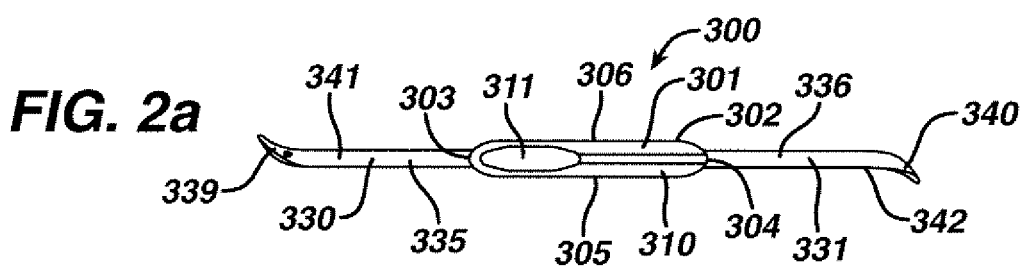
FIGS. 2a and 2b are top and side perspective views respectively of an instrument particularly suitable for aiding in implantation of the implant of FIG. 1.
Figure 2B:
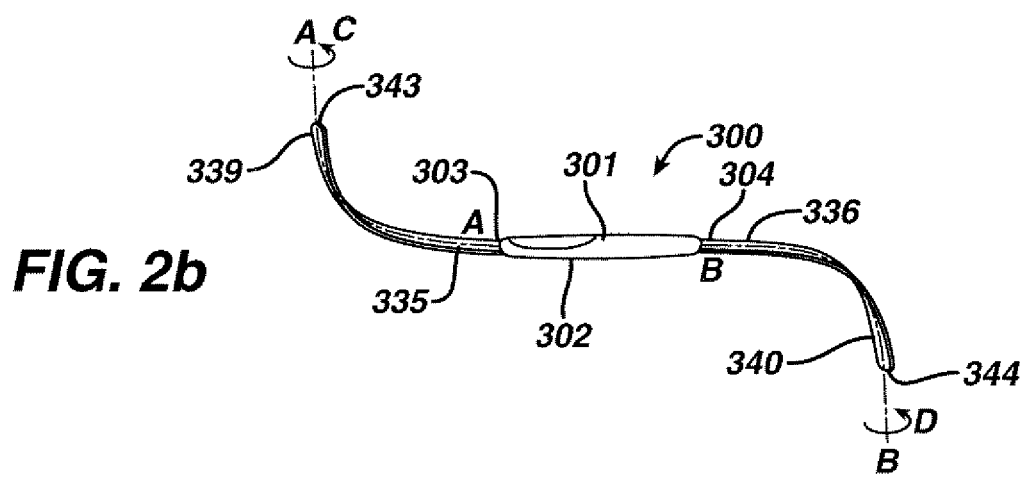

The open end of the pocket is capable of receiving the end of an implantation instrument or device to facilitate implantation of the implant as will be described further below. An implantation device particularly suited for implantation for an anterior repair is illustrated in FIGS. 2a-2b, which are top and side perspective views respectively. The instrument 300 includes a grip portion 310 suitably configured for gripping the instrument. The grip portion 310 has a top side 301, a bottom side 302, first and second end sides 303, 304, and front and rear sides 305, 306. The grip portion is preferably comprised of polycarbonate or any biocompatible plastic, and may include one or more grip regions 311 configured to received a users finger or thumb to facilitate handling of the instrument.

The instrument 300 further includes a first substantially rigid extension arm 330 extending laterally outward from the first end side 303 of the grip portion, and a second substantially rigid extension arm 331 extending laterally outward from the second end side 304 of the grip portion. The arms may be made of any suitable biocompatible material having sufficient stiffness for implantation procedures as described below, such as stainless steel. Although the first and second extension arms are described herein as extending outwardly from the first and second sides of the grip portion, it is to be understood that the first and second extension arms may be one unitary structure extending through the grip portion (i.e., a polymeric grip portion formed around a central portion of the unitary structure), and reference to "first and second" extension arms is not to be construed as requiring two separate extension arms separately secured to the grip portion although it could. Each of the first and second extension arms extend outwardly along first and second longitudinal axes, which for the purposes of the present application is defined as a line extending along the length of the extension arm and substantially centrally located relative to the cross-section of the extension arm, as shown by dotted lines A-A and B-B in FIG. 2b.

Each of the first and second extension arms further includes a substantially straight portion 335, 336 and a distal portion 339, 340. The substantially straight portions 335, 336 are proximal to the first and second 303, 304 end sides of the grip portion. Within the first and second substantially straight portions 335, 336, the extension arms lie substantially within a single first plane, and the same plane as one another. The distal portions 339, 340 extend from the substantially straight portions to first and second distal ends 343, 344 respectively. Within the first distal portion 339 of the first extension arm, the extension arm extends upwardly away from the first plane, and also rotates counterclockwise about longitudinal axis A-A as shown by arrow C in FIG. 2b. Within the distal portion 340 of the second extension arm, the extension arm extends downwardly away from the first plane, and also rotates counterclockwise about longitudinal axis B-B as shown by arrow D in FIG. 2b. Preferably, the first and second distal ends are blunt, with a substantially flat edge.

Figure 8:
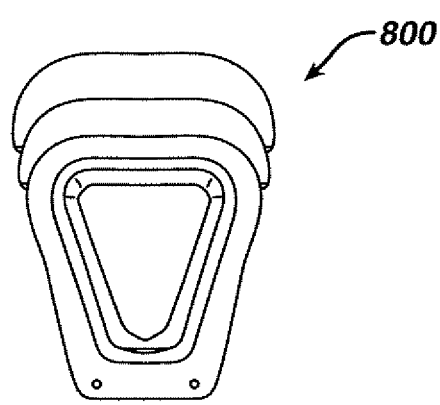

As indicated, the implant of the present invention is intended for use in various pelvic floor repair procedures, and may be used in connection with a intra-vaginal splint of the type described in detail in co-pending U.S. patent application Ser. Nos. 11/258,441, 11/334,966 and 10/534,930, the disclosures of which are incorporated herein by reference in their entirety, to aid in temporarily holding the implant in place during initial tissue ingrowth into the implant. One example of such a splint 800 is illustrated in FIG. 8. Exemplary procedures for implanting the implant will now be described in detail.

Figure 4A:
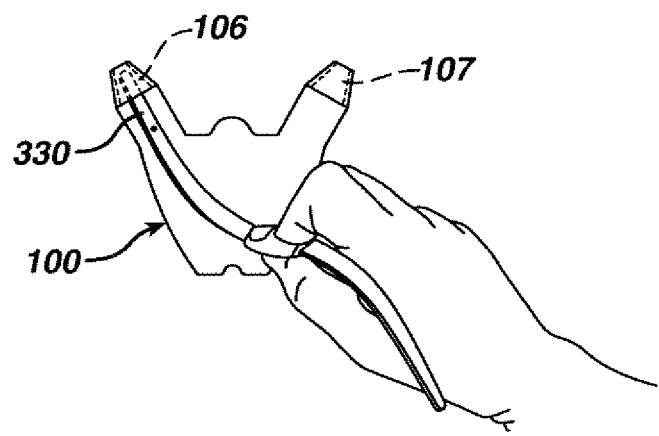
FIGS. 4a-4d illustrate various aspects of a method for implanting the implant of FIG. 1 for an anterior repair.
Figure 4B:
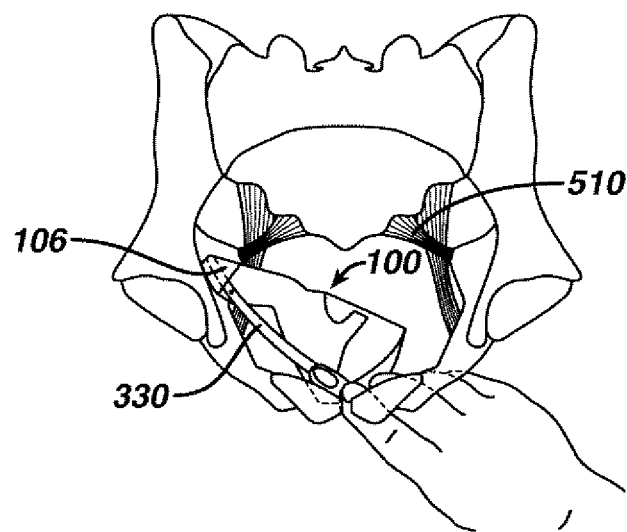

The implant as described and illustrated herein has particular application for repairing anterior, posterior, and/or apical vaginal defects. For an anterior repair when reinforcement of only the anterior vaginal wall is needed, the implant 100 is intended to be placed between the urinary bladder 500 and the upper ⅔ of the vagina 501 (see FIG. 4d), with the central body portion extending laterally approximately at the level of the arcus tendineus fascia pelvis (ATFP), the approximate position of which is illustrated by reference numeral 521 in FIG. 4c. The anterior vaginal epithelium is first dissected off the bladder, dissecting the full thickness of the vaginal wall and avoiding separation into two layers. The dissection is continued laterally toward the pelvic sidewall (also illustrated approximately by 521) and to the depth of the ischial spine 522. Further dissection is done to create channels for placement of the strap-like extensions 102, 103 of the implant 100, with the extensions preferably being placed flush against pelvic side wall and parietal fascia of the obturator internus muscle 523 (FIG. 4b). The dissection on each side should create a channel anterior and superior to the ischial spine and superficial to the ATFP, the obturator internus muscle, and parietal fascia.

Figure 3A:
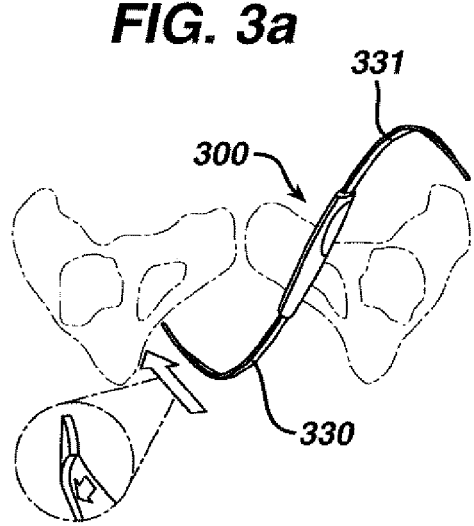
FIGS. 3a-3d illustration the orientation of the instrument of FIGS. 2a-2b when used to aid in implantation of the implant of FIG. 1.
Figure 3B:
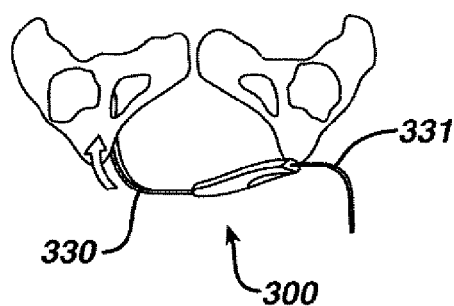
Figure 3C:
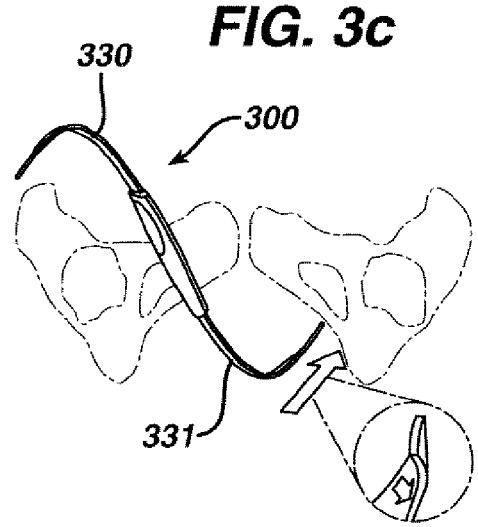
Figure 3D:
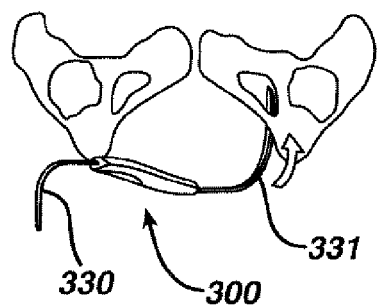
Figure 4C:
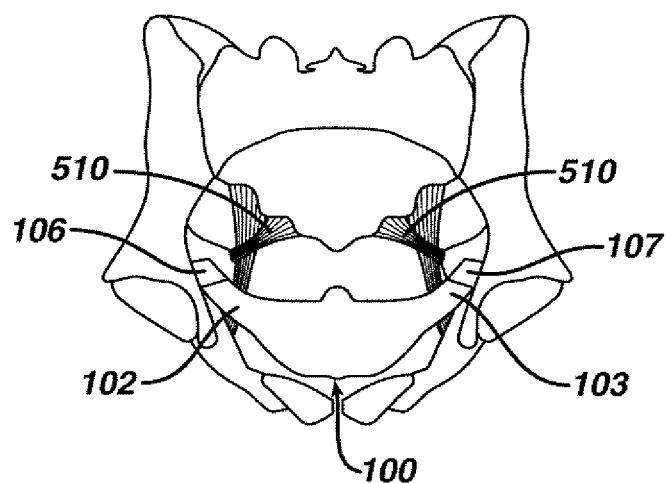
Figure 4D:
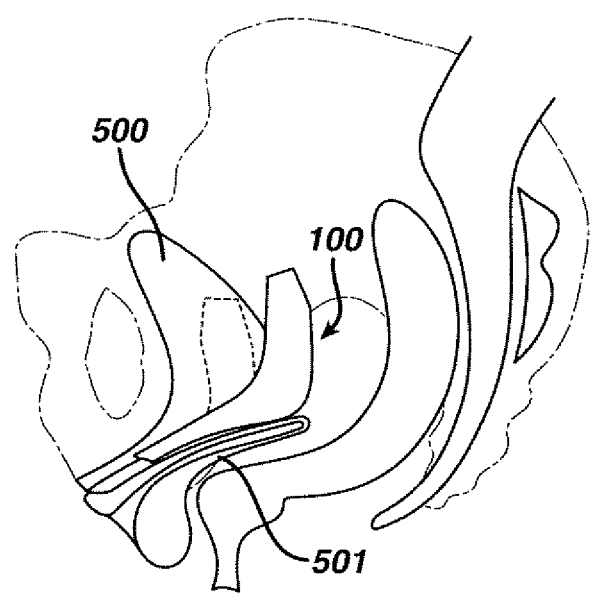

Following dissection, the implant 100 is placed over the pre-vesical tissue with the straps inserted into each right and left channel created by the dissection anterior and superior to the ischial spine as described above. Implantation of the mesh and strap-like extension portions may be facilitated by using the instrument 300 illustrated in FIGS. 2a-2b and described herein. As shown in FIG. 4a, the distal end 343 of the first extension arm 330 is inserted into the first pocket 106 of the implant, with the pocket facing upwards. Visual indicators 524, such as the arrows shown in FIGS. 3a and 3c, may be used to ensure proper orientation of the instrument. The instrument and implant is then inserted through the channel described above (as shown in FIG. 4b, which, for the purposes of clarity does not illustrate most tissue) on the right side of the patient's body until the grip portion 301 comes in contact with the labia majora on the contra-lateral side. The grip portion is then lowered until approximately parallel to the floor, such that the distal tip is adjacent to and in contact with the internus muscle. The instrument is then removed, and the distal end 344 of the second extension arm 331 inserted into the second pocket 107, with the combination inserted into the second channel formed on the left side of the patient's body. FIGS. 3a and 3b further illustrate positioning of the instrument 300 during implantation on the right side of the body. For illustrative clarity, neither the implant nor soft tissue structures are shown. FIGS. 3c and 3d similarly illustrate positioning of the instrument during implantation on the left side of the body. When the instrument is subsequently removed, the implant should be placed as illustrated in FIGS. 4c and 4d. The central body portion 101 of the implant is then positioned loosely over the underlying vaginal tissue. The vaginal epithelium is then closed in a suitable manner.

Figure 5A:
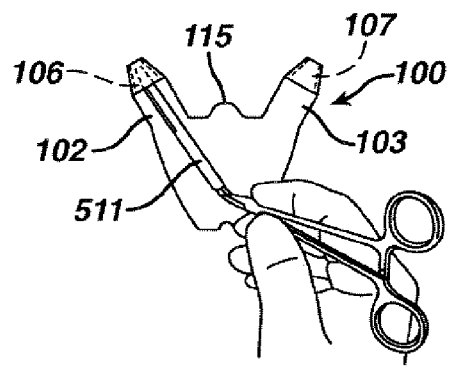
FIGS. 5a-5d illustrate various aspects of a method for implantation of the implant of FIG. 1 for a posterior repair.
Figure 5B:
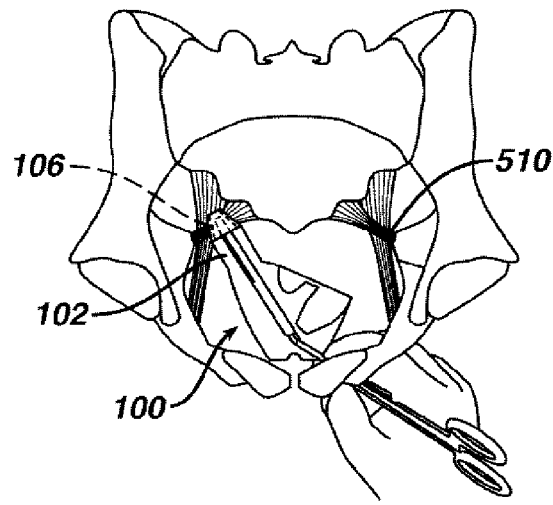
Figure 5C:
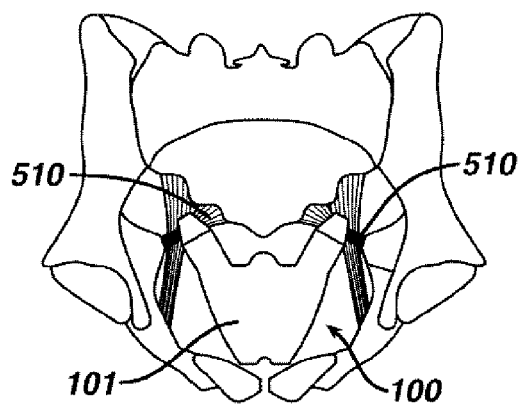
Figure 5D:
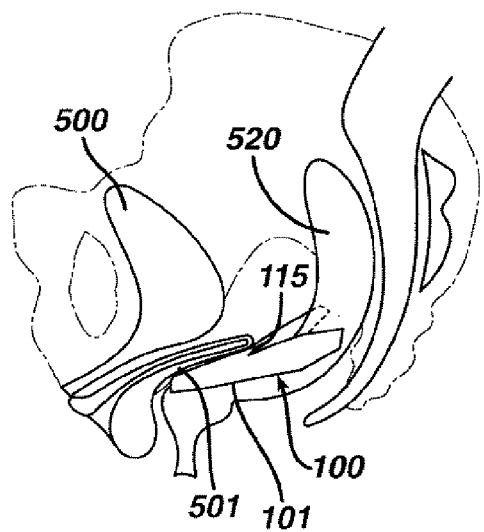

For a posterior repair (when reinforcement of only the posterior vaginal wall is needed), the full thickness of the posterior vaginal epithelium is first dissected off the pre-rectal tissue (rectum 520 illustrated in FIG. 5d). The dissection for the central body portion 101 is continued laterally on each side to the levator ani muscle at a depth to the level of the ischial spine, and then channels are created through each of the rectal pillars (not shown) and onto, but not through, each sacrospinous ligament 510. The dissected channels into which the strap-like extension portions of the implant are placed will ultimately help secure the implant after tissue ingrowth.

The implant is then placed over the pre-rectal tissue with the strap-like elements 102, 103 inserted into each right and left channel created by the dissection towards each sacrospinous ligament 510. The strap-like elements may be inserted with the aid of any suitable surgical instrument 511 (instrument 300 of the configuration shown in FIGS. 2a and 2b is not particularly suitable for posterior repair placement) one end of which is received within the pockets 106, 107 of the strip-like elements in a similar manner as described above. The ends of the strap-like elements are positioned so that they abut, but do not penetrate, the sacrospinous ligaments 510. Optionally, either before or after the insertion of the strap-like elements, the tab element 115 can be tacked (by suture or other fastener type element) to the apex of the vagina 501a as shown in FIG. 5d. Similarly, the implant may further be tacked down to pre-rectal tissue along the anterior edge. The centrally located tab element and recess help the surgeon to visually verify that the implant has been centrally aligned.

The central body 101 of the implant is then positioned loosely over the underlying vaginal fascia, and care is taken to ensure that the strap-like extensions are not folded or twisted. Depending on the vaginal dimensions, or the amount of lateral dissection, the central body may require trimming. The posterior vaginal wall epithelium is then closed over the implant, with final placement of the implant as illustrated in FIGS. 5c and 5d.

Figure 6A:
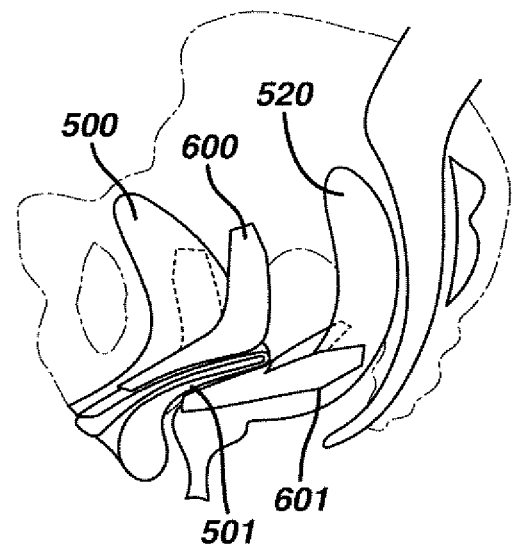
FIGS. 6a and 6b illustrate placement of two implants for a combination anterior/posterior repair.
Figure 6B:
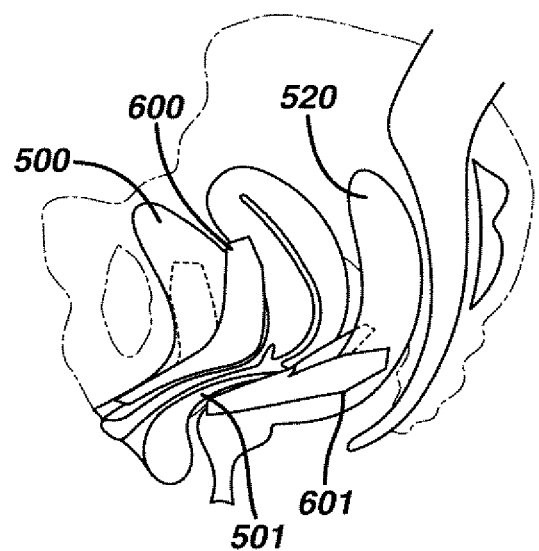
Figure 7:
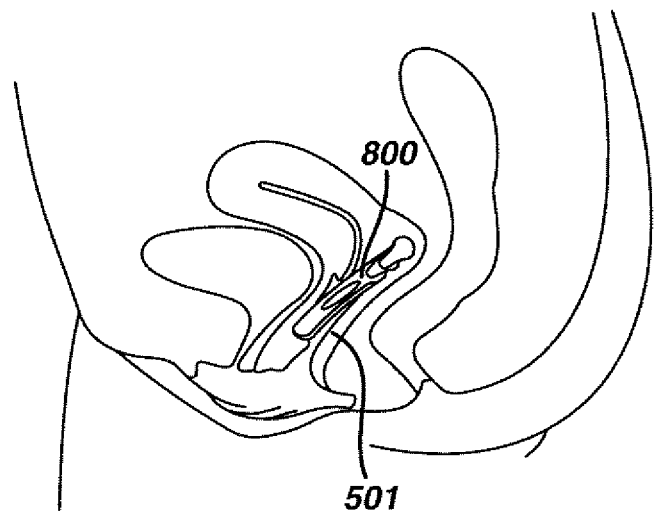
FIGS. 7 and 8 illustrate an exemplary vaginal splint and placement thereof that can be used in connection with the implants of the present invention.

If both anterior and posterior vaginal wall reinforcement is needed, two implants of the type described herein can be used, with the first 600 placed as described above for the anterior repair and the second placed 601 as described above for the posterior repair. The anterior repair should be performed first. Final placement of the first and second implants is shown in FIGS. 6a (hysterectomy) and 6b (no hysterectomy).

As indicated previously, the implants described above can be used in conjunction with a vaginal splint to aid in maintaining the proper positioning of the implants during initial tissue ingrowth. A splint 800, such as the exemplary splint shown in FIG. 8, is inserted into the vagina 501 as shown in FIG. 8, and as described in detail in co-pending U.S. application Ser. Nos. 11/258,441, 11/334,966 and 10/534,930, which have been incorporated herein by reference in their entirety. Following insertion the balloon is expanded, and the splint is left in place for approximately 1-2 days, after which it can be deflated. The splint can then remain in place for approximately 3-4 weeks to ensure that proper tissue ingrowth has occurred.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A surgical kit comprising:
    an implantation instrument comprising a straight grip portion extending along a single longitudinal axis, and having a top side, a bottom side, first and second opposing end sides, and front and rear sides;
    a first rigid extension arm projecting outwardly from the first end side of the grip portion along a first longitudinal axis, the first extension arm having a flat, uniform cross-section along a length thereof; and
    a second rigid extension arm projecting outwardly from the second end side of the grip portion in a direction opposite that of the first rigid extension arm along a second longitudinal axis, the second extension arm having a flat, uniform cross-section along a length thereof,
    wherein the first rigid extension arm has a straight portion adjacent the grip portion wherein the first extension arm lies within a first plane and wherein the longitudinal axis of the straight portion is coincident with the longitudinal axis of the grip portion, and a distal portion extending from the straight portion to a first distal end along a length of which the first extension arm extends upward relative to the first plane and rotates about its first longitudinal axis;
    wherein the second rigid extension arm has a second straight portion adjacent the grip portion wherein the second extension arms lies within the first plane and wherein the longitudinal axis of the straight portion of the second extension arm is coincident with the longitudinal axis of the grip portion, and a second distal portion extending from the straight portion to a second distal end along a length of which the second extension arms extends downward relative to the first plane and rotates about its longitudinal axis; and an implantable mesh having at least one pocket having an open end, wherein the distal end of the first and second extension arms are slidably receivable within the pocket through the open end thereof.

2. The surgical kit according to claim 1, wherein the distal portion of the first extension arm rotates counterclockwise about its first longitudinal axis.

3. The surgical kit according to claim 2, wherein the distal portion of the second extension arm rotates counterclockwise about its second longitudinal axis.

4. The surgical kit according to claim 1, wherein the distal portion of the first and second extension arms each rotate less than 90 degrees.

5. The surgical kit according to claim 1, wherein the distal portion of the first and second extension arms each rotate less than 45 degrees.

6. The surgical kit according to claim 1, wherein the longitudinal axes of the first and second extension arms at the first and second distal ends respectively are perpendicular to the first plane.

7. The surgical kit according to claim 1, wherein the first and second extension arms have identical lengths, cross-sections, and straight portions.

8. The surgical kit according to claim 7, wherein the cross-section of the first and second extension arms is rectangular.

* * * * *